(12) United States Patent
Prabhakarpandian et al.

(10) Patent No.: US 8,380,443 B2
(45) Date of Patent: *Feb. 19, 2013

(54) MICROFLUIDIC ASSAY FOR CHARACTERIZATION OF THE LEUKOCYTE ADHESION CASCADE

(75) Inventors: Balabhaskar Prabhakarpandian, Madison, AL (US); Kapil Pant, Madison, AL (US); Shivshankar Sundaram, Tampa, FL (US)

(73) Assignee: CFD Research Corporation, Huntsville, AL (US)

( * ) Notice: Subject to any disclaimer, the term of this patent is extended or adjusted under 35 U.S.C. 154(b) by 414 days.

This patent is subject to a terminal disclaimer.

(21) Appl. No.: 12/612,573

(22) Filed: Nov. 4, 2009

(65) Prior Publication Data

US 2010/0112550 A1    May 6, 2010

Related U.S. Application Data

(63) Continuation-in-part of application No. 11/393,715, filed on Mar. 31, 2006, now Pat. No. 7,725,267.

(51) Int. Cl.
*G01N 33/48* (2006.01)
(52) U.S. Cl. .......................................... 702/19
(58) Field of Classification Search ............... 702/19
See application file for complete search history.

(56) References Cited

U.S. PATENT DOCUMENTS

| | | | | |
|---|---|---|---|---|
| 6,473,698 B1 * | 10/2002 | Albert et al. | ................ | 702/45 |
| 2002/0160505 A1 | 10/2002 | Groves et al. | ............. | 435/287.1 |

FOREIGN PATENT DOCUMENTS

WO    WO-2004020341 A2    11/2004

OTHER PUBLICATIONS

Shevkoplyas et al. Microvascular Research (2003) 65:132-136.
Weigle et al. "Lab-on-a-chip for drug development" Advanced Drug Delivery Reviews 55:349-377 (2003).
Long et al. "Numerical study of blood flow in an anatomically realistic aorto-iliac bifurcation generated from MRI data" Magnetic Resonance in Medicine 43(4):565-76 (2000) Abstract.
Lim et al. "Fabrication of Microfluidic Mixers and Artificial Vasculatures Using a High-Brightness Diode-Pumped Nd:YAG Laser Direct Write Method" Lab Chip (2003) 3:318-323.
Tan et al. "Microfluidic Patterning of Cellular Biopolymer Matrices for Biomimetic 3-D Structures" Biomedical Microdevices (2003) 5:235-244.
Runyon et al. "Minimal Functional Model of Hemostatis in a Biomimetic Microfluidic System" Angew. Chem. Int. Ed. (2004) 43:1531-1536.

* cited by examiner

*Primary Examiner* — Jerry Lin
(74) *Attorney, Agent, or Firm* — Maschoff Gilmore & Israelsen (57) ABSTRACT

An apparatus and method for identifying and screening for agents affecting the leukocyte adhesion cascade (LAC) encompassing rolling, adhesion and migration comprises an optically clear, plastic microfluidic chip comprising flow channels with diameters in the range of 10-500 μm. The flow channels are coated with endothelial cells and at least a portion of the flow channels contains 1-30 μm sized openings, optionally filled with a native or synthetic extracellular matrix, that allow leukocyte migration into one or more tissue spaces.

27 Claims, 8 Drawing Sheets

MICROFLUIDIC ASSAY FOR CHARACTERIZATION OF THE LEUKOCYTE ADHESION CASCADE

CROSS-REFERENCE TO RELATED APPLICATIONS

This application claims priority under 35 U.S.C. 120 to application Ser. No. 11/393,715, filed Mar. 31, 2006.

STATEMENT REGARDING FEDERALLY SPONSORED RESEARCH

Not Applicable

BACKGROUND OF THE INVENTION

1. Field of the Invention

The present invention relates to an in vitro assay for characterization of the leukocyte adhesion cascade. More specifically, the invention relates to a leukocyte adhesion and migration assay using a microfluidic apparatus.

2. Description of Related Art

The leukocyte adhesion cascade, a multistep process mediated by a series of receptor-ligand interactions, is important to many physiological and pathophysiological processes of the body. A number of in vitro models have been developed to study different aspects of the leukocyte adhesion cascade and to develop and test anti-inflammatory agents and other drugs. Flow chambers have been developed to study rolling and adhesion phenomena, and Boyden and transwell chambers have been used for migration studies.

Flow chambers provide physiological shear but cannot model transmigration. Transwell and Boyden chambers do not account for fluid shear and size/topology observed in-vivo or provide real-time visualization of leukocyte migration, measure leukocyte migration semi-quantitatively, and are labor intensive. No experimental model currently resolves rolling, adhesion and migration in a single assay. As a consequence, understanding of the leukocyte adhesion cascade and anti-inflammation drug development has been limited. For example, a leukocyte migration inhibitor in Boyden chambers may fail to work in realistic flow shear. The method and apparatus of the present invention provide a rapid assay for anti-inflammatory markers and drugs targeted to affect the leukocyte adhesion cascade.

BRIEF SUMMARY OF THE INVENTION

The apparatus and method described herein address a need in the art for an assay capable of identifying and screening for agents affecting the leukocyte adhesion cascade (LAC) encompassing rolling, adhesion and migration. The LAC assay device comprises an optically clear, plastic microfluidic chip comprising flow channels with diameters in the range of 10-500 µm. The lumenal walls of the flow channels are coated with endothelial cells and the walls of at least a portion of the flow channels may contain 1-30 µm sized openings, pores, or gaps, optionally filled with a native or synthetic extracellular matrix, that allow leukocyte migration into one or more tissue spaces. The flow channels may be linear or bifurcating channels, may form an idealized microvascular network (IMN), or they may be present in the form of a synthetic microvascular network (SMN). In contrast with current in-vitro models, this device resolves and facilitates direct assessment of individual steps in the leukocyte adhesion cascade including rolling, firm arrest (adhesion), spreading, and extravasation of the leukocytes into the extra-vascular tissue space. The present assay may include quantitative end point measurement, real-time visualization of cell migration, and automation of assay method steps.

DETAILED DESCRIPTION OF THE INVENTION

Definitions

A "synthetic microvascular network" (SMN) is a man made network comprising a plurality of interconnected, non-linear flow channels that form geometrical features and have fluid flow properties found in physiological microvascular networks. The flow channels form intersecting networks that may be arranged to form synthetic analogs of an arteriole, capillary, venule sequence. A flow channel in a SMN possesses one or more geometric characteristics of physiological microvascular vessels: variable cross-sectional shapes, variable cross-sectional areas, convolutions, turns, and anastomoses. A network of linear flow channels joining at angles, for example, is not a SMN. Straight channels or other channels having non-physiological geometries may be used to link a synthetic microvascular network to other components of a microfluidic chip. These channels, however, are not a part of the microvascular network.

As used herein, the term "idealized" in association with a microfluidic network, junction, or bifurcation is used to describe a synthetic network, junction, or bifurcation consisting of straight microfluidic channels joined at acute, right, or obtuse angles.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

A "microfluidic chip" is constructed using techniques employed in the semiconductor industry such as photolithography, wet chemical etching, thin film deposition, laser patterning and soft lithography using polymeric substrates. This is in contrast to microfluidic systems formed in gels made of proteins, chitosan, proteoglycans, and/or other extracellular matrix components. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

Figure 1:
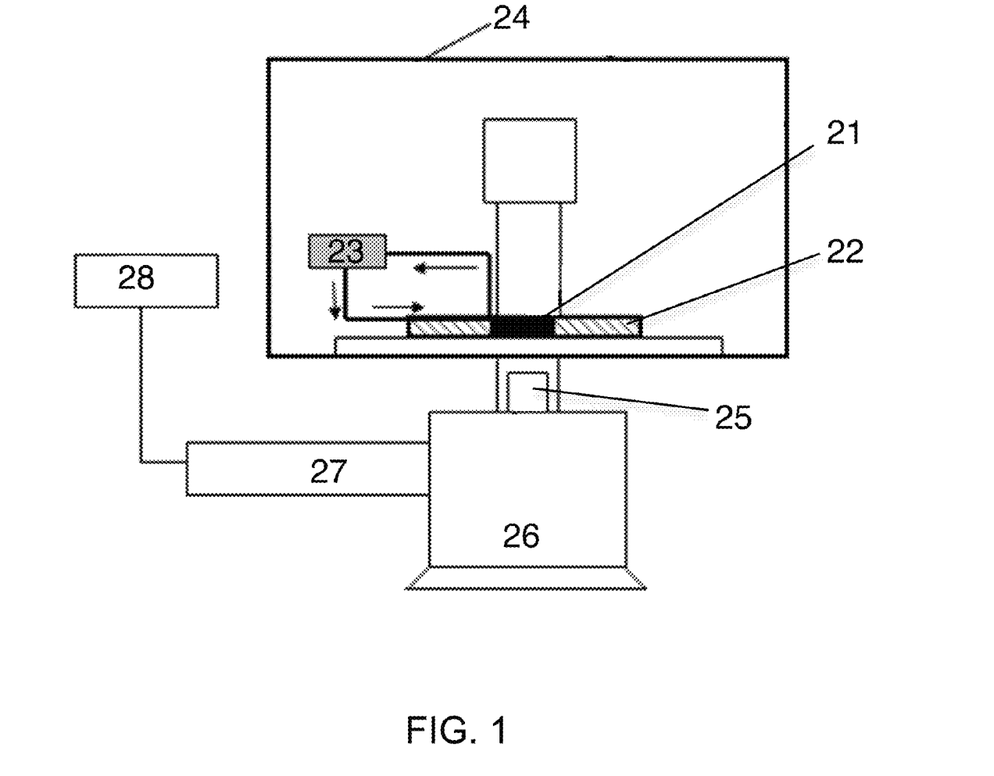
FIG. 1 is a drawing of an assay system in which a solution is passed once or optionally recirculated into the microfluidic device.

Assay System:

FIG. 1 shows an exemplary system for performing Leukocyte Adhesion Cascade assays according to the present invention. A microfluidic chip (21) is placed on an automated stage device (22) and connected to a pump (23) that is connected to inlets, outlets, and, optionally, ports on the microfluidic chip (21). The microfluidic chip (21) is preferably contained within an incubation chamber (24) and is positioned over the objective lens (25) of a brightfield, phase contrast or fluorescent microscope (26). Optical means such as a CCD camera or video camera (27) are used to visualize cells within the microfluidic chip (21). The camera (27) is in communication with a computer (28) for data collection and control of microscope (26), camera (27) and microscope mounted accessories. Fluid may be recirculated through the microfluidic chip (21) as shown in the figure or may be pumped in a single pass mode from the pump (23) to a waste reservoir (not shown).

Figure 2:
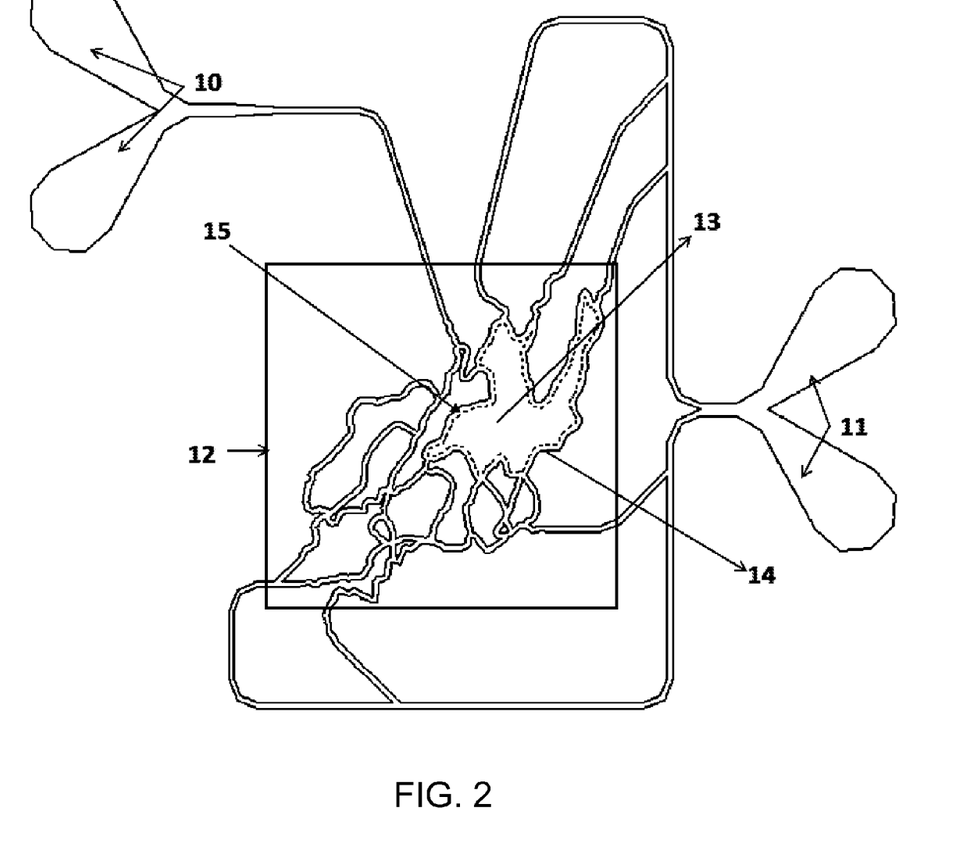
FIG. 2 is a drawing showing the components of a microfluidic chip derived using SMN for performing Leukocyte Adhesion Cascade assays.

Microfluidic Chip Comprising a SMN:

Components included in a microfluidic chip comprising a synthetic microvascular network are shown in FIG. 2. The SMN (12) comprises a plurality of interconnected, nonlinear flow channels (14), in fluid communication with one or more inlets (10) and one or more outlets (11). One or more extravascular/tissue spaces (13) are separated from and in fluid contact with flow channels of the SMN via gaps or pores (15) having dimensions of between 1 and 30 micrometers in the wall of at least one flow channel (14) adjacent to at least one tissue space (13). The cross-section may be a diameter in the case of circular pores or may be the length of the longest side for rectangular gaps.

Obtaining Geometries for SMNs:

Maps of complete microvascular networks are constructed from a collage of arterioles, capillaries and venules. The entire network is digitized by tracing each vessel on the assembled collage in an AutoCad Map® using a computerized drawing board (e.g., Drawing Board III®, CalComp).

After a network is digitized, an AutoCad Map® cleanup routine is used to ensure all vessels are properly connected at their common nodes. A tolerance value is set which distinguishes between common nodes and neighboring end points. Each vessel is graphically represented by a polyline consisting of a series of straight lines connected through vertices. The system compares the distance between successive vertices in a polyline to the set tolerance value. The vertex is removed from the polyline if the distance is below the set tolerance value. Images of physiological microvascular networks for use in obtaining geometries may also be obtained using digital photography (e.g. retinal imaging).

Reconstructed "Averaged" Microvascular Networks:

Averaged or nominal microvascular networks are based on the geometries of at least two actual microvascular networks and can be used, for example, to translate a 3-dimensional network into a 2-dimensional network. The images are analyzed as described above and subjected to a detailed morphological analysis to yield statistical data of morphometric parameters such as ratios of parent to daughter vessel diameters, branching angles, distances between branches, rations of branch length to branch channel diameter, tortuosity, bifurcation branch density, and recombining branch density. Averaged microvascular networks can be generated by using averaged morphometric data and/or stochastic sampling of probability density functions for morphometric data. Averaged microvascular networks may be generated using values selected from a variety of statistical distributions for individual morphometric parameters. The values used need not be "average," "mean," or "median" values for measured morphometric parameters.

Figure 3:
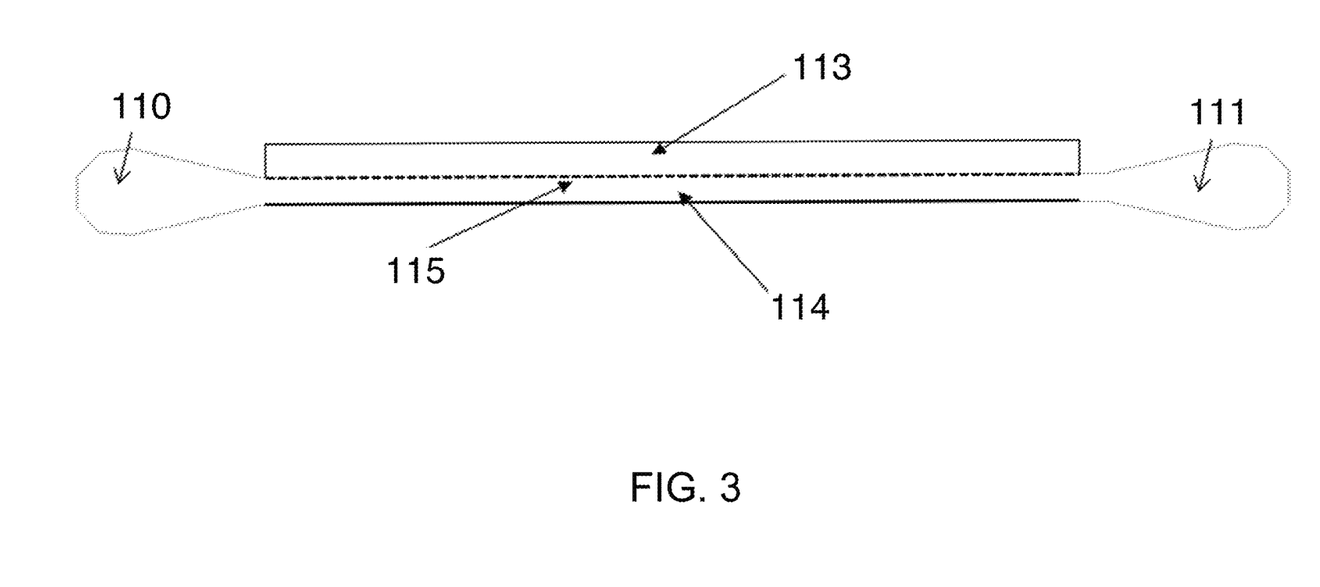
FIG. 3 is a drawing showing the border between a tissue space and flow channel in an IMN.
Figure 4:
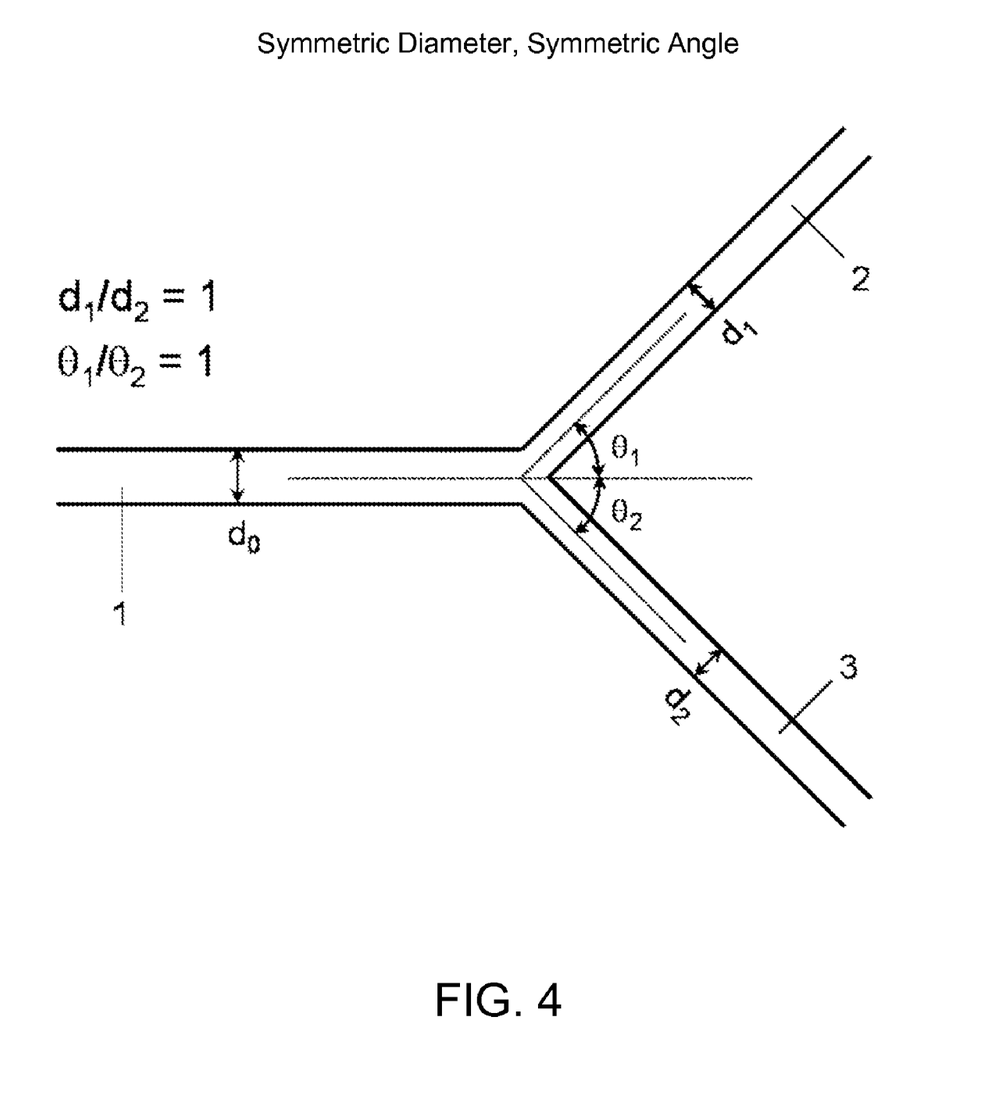
FIG. 4 shows a symmetric bifurcation with symmetric daughter diameters.
Figure 5:
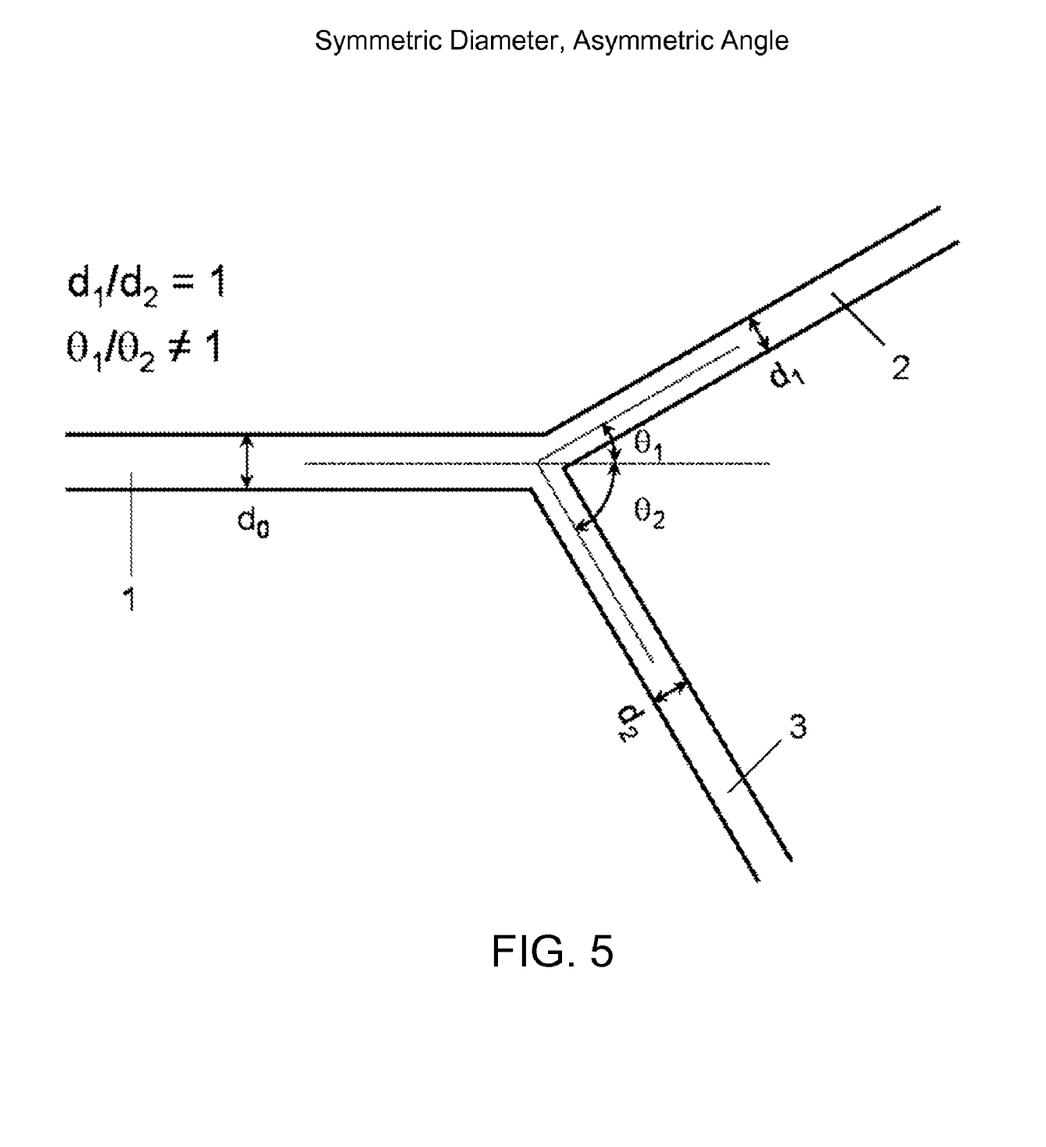
FIG. 5 shows an asymmetric bifurcation with symmetric daughter diameters.
Figure 6:
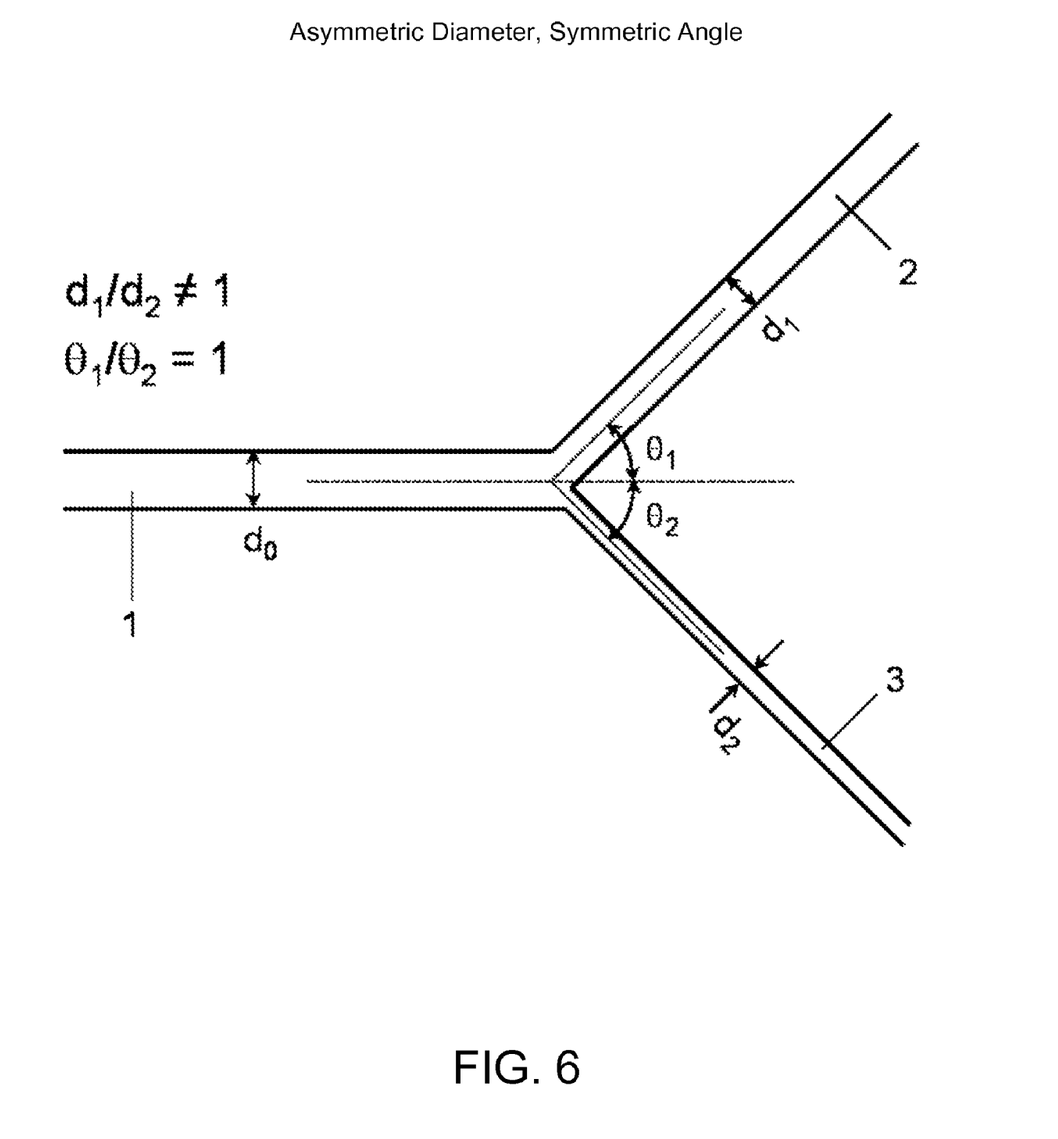
FIG. 6 shows a symmetric bifurcation with asymmetric daughter diameters.
Figure 7:
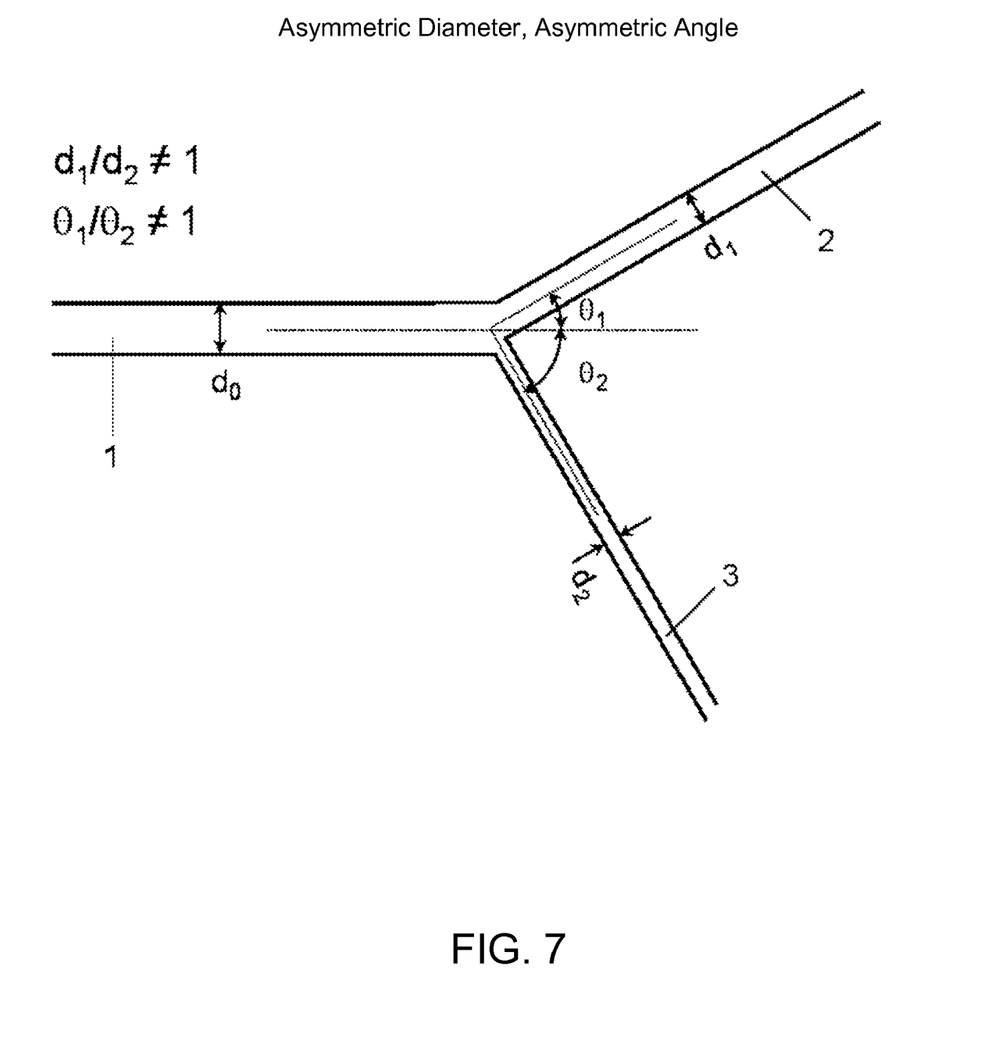
FIG. 7 shows an asymmetric bifurcation with asymmetric daughter diameters.

Microfluidic Chip Comprising an IMN:

FIG. 3 shows the boundary between a straight flow channel (114) and a tissue space (113) in an IMN embodiment of a microfluidic chip. Flow channel (114) is in fluid communication with inlet (110) and outlet (111) and borders tissue space (113) along an area of 1-30 μm gaps (115) with tissue space. Flow channel (114) may be a single, straight channel as shown or may be a portion of a bifurcated channel, in which case fluid communication with inlet (110) and outlet (111) may not be direct, as shown, but may be through additional flow channels.

Idealized microvascular networks comprise single or multiple bifurcations and/or junctions consisting of linear parent and daughter channels having rectangular or circular or semi-circular cross-sections that diverge or converge at angles of between 15° and 135°. The diameters or cross-sections of the channels are between 10 μm and 500 μm. The bifurcations and junctions are categorized as illustrated in FIG. 4 through FIG. 7. In the figures, $d_o$, $d_1$, and $d_2$ represent the diameters of the parent (1) and first and second daughter channels (2, 3), respectively. $\theta_1$, and $\theta_2$ represent the angles formed between the parent channel (1) and the first and second daughter channels (2, 3), respectively. "Diameter" in the context of channels having a rectangular cross-section refers to the longest cross-sectional distance and cross-sectional area is calculated as width×depth. For channels having circular cross-sections, cross-sectional area is calculated as diameter×diameter×π/4. For channels having semi-circular cross-sections, "diameter" refers to the longest cross-sectional dimension and cross-sectional area is calculated as diameter×diameter×π/8.

Figure 8:
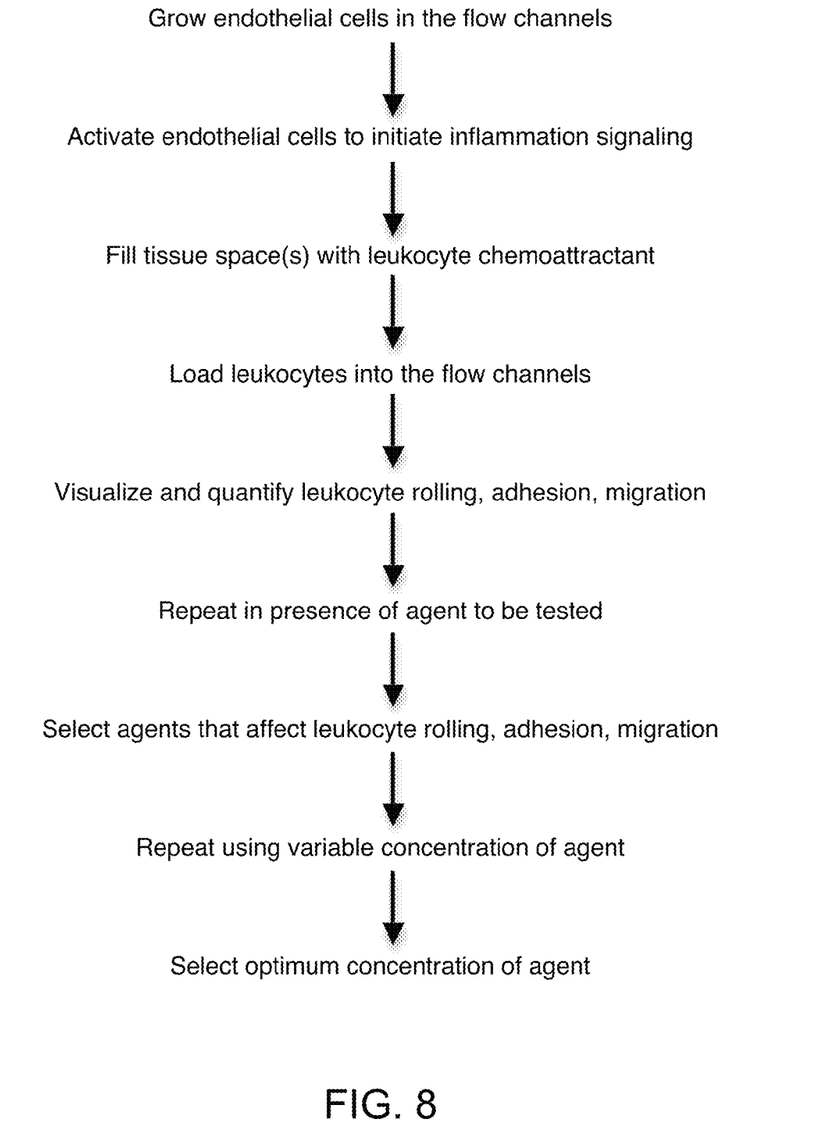
FIG. 8 is a flow chart showing the basic method steps for identifying an agent that modulates leukocyte adhesion, rolling, and/or migration from the microvasculature.

General Assay Method:

One exemplary set of method steps for a LAC assay according to the present invention is outlined in FIG. 8. The flow channels are coated with a layer of cells, preferably a confluent layer of cells. The cells are preferably primary endothelial cells or a cultured endothelial cell line. The flow channels may first be coated with a substance to facilitate cell adhesion, such as extracellular matrix proteins or proteoglycans. In most cases, the layer of endothelial cells is activated before leukocytes are introduced into the device. The cytokine, TNF-α is commonly used for activation of endothelial cells but any substance capable of activating the cells may be used. Pores or pores and extravascular tissue spaces may be filled with a gel such as Matrigel® to provide a medium through which leukocytes can migrate. For stimulating leukocyte migration, a source for a leukocyte-attracting cytokine or other leukocyte chemoattractant may be introduced into at least one extravascular space. A suspension of leukocytes is introduced into the device and allowed to circulate or allowed to incubate, depending on the purpose of the assay. Leukocytes may be recirculated through the device at a single or multiple flow rates to assess the effect of shear forces on leukocyte rolling, adhesion, and/or migration modulation. The locations of leukocytes and numbers of leukocytes in different locations within the device over time are captured by digital camera or other optical means and stored in a computer. The degree of leukocyte rolling, adhesion, and/or migration modulation is measured by comparing the numbers of leukocytes located at various positions in the device over time, providing end point and kinetic values for leukocyte cascade activation. Leukocytes may be introduced into the chip at desired time points following activation to reproduce the complete adhesion cascade. One or more chemoattractants may be introduced into one or more extravascular tissue spaces to stimulate migration. Rolling, adhesion and migration of leukocytes into the one or more extravascular tissue spaces may be captured in real-time by scanning the entire network. Drug screening may be performed, for example, by the injection of potential cascade inhibitors to analyze the effect on adhesion and migration.

EXAMPLE 1

Leukocyte Rolling and Adhesion on Activated Endothelium

A microfluidic chip comprising a SMN is degassed by vacuum for 5 minutes and placed on an automated stage that is mounted on a microscope equipped with a camera. The entire chamber is housed in an incubation chamber configured to maintain temperature, $CO_2$ concentration, and humidity.

Sterile phosphate buffered saline is injected into an inlet port (10) at a flow rate of 10 µl/min for 10 minutes to prime the chip. Following priming, fibronectin (50 µg/ml) is introduced into the inlet port (10) for 5 minutes at a flow rate of 10 µl/min. The fibronectin solution is allowed to incubate in the device for 2 hrs at room temperature to completely saturate all the surfaces. Primary endothelial cells at a concentration of $5 \times 10^6$ cells/ml in media are introduced into the inlet port (10) and incubated at 37° C. and 5% $CO_2$. Media is replaced every 24 hr until the cells are confluent in the device. The confluent endothelial cells are activated by perfusion with TNF-α at a concentration of 10 U/ml for 4 hr or 24 hr.

Leukocytes at a concentration of approximately $10^5$-$10^6$ cells/ml are perfused into the device via inlet (10) at a flow rate corresponding to a shear rate of 500 $sec^{-1}$ for 30 minutes using a peristaltic pump for looping or via a syringe pump for single pass. Software is used to automatically control the stage, camera and the timing for image acquisition and scanning of the entire device. Rolling and adhered leukocytes are imaged and quantified using image analysis software.

Complex flow in the device may be characterized experimentally or using computational fluid dynamics (CFD) simulations in advance of the assay and stored in a database. The experiment may be repeated using flow rates corresponding to different shear rates or the device can be designed to incorporate regions providing different shear rates at the same flow rate at the inlet or inlets to allow data collection producing a curve of number of rolling cells vs. shear rate or number of adhered cells vs. shear rate.

The experiment may be repeated in the presence of one or more agents such as drug candidates to identify one or more drugs, alone or in combination, that affect, either positively or negatively, leukocyte rolling and/or adhesion based upon the relative numbers of leukocytes counted as rolling or adherent.

EXAMPLE 2

Leukocyte Rolling, Adhesion, and/or Migration on Activated Endothelium

The microfluidic chip is prepared and flow channels coated by a confluent layer of endothelial cells as in Example 1. The extravascular tissue spaces of the device are filled with a solution containing a chemoattractant such as N-Formyl-L-methionyl-L-leucyl-L-phenylalanine (fMLP) diluted in cell media to a concentration of 100 nM. Following the injection of fMLP, leukocytes are introduced into the inlet port of the device and allowed to adhere to the endothelial cells using the protocol in Example 1. Following 30 minutes of the cell flow, the flow is switched to a cell free media to wash off circulating unbound leukocytes. Cell media is maintained for 24 hr by circulating perfusion at a selected shear rate of 120 $sec^{-1}$. The device is repeatedly scanned and imaged, as in Example 1, every 30 minutes for 24 hr. Any cells that leave the vessel area (lumen of the network) and migrate into the tissue area are digitally photographed and counted. At the end of the respective time point, the individual images are merged together to create a time-lapse composite image to quantify the number of cells that have migrated. A plot of cells migrated vs. the local shear rate may also generated using data from successive or parallel variable shear rate conditions. In addition, the geometric features of the adhesion sites can be recorded to allow for distinction between (a) shear only, or (b) shear and geometry based adhesion/migration. Fluorescent live cell dyes may be used to supplement phase contrast microscopy to aid in tracking migrated cells.

The experiments described in Example 2 may also be performed using a microfluidic chip in which the pores in the walls of the flow channel separating the vascular lumen from the extravascular tissue space are filled with a gel, such as Matrigel®. In this case, Matrigel® is placed into pores desired locations of the device.

Matrigel® is mixed to a final concentration of 1 mg/ml in serum free cold media. The Matrigel® solution is injected into the prescribed tissue areas of the device. A small amount of vacuum is applied in the channels to aid in movement of the Matrigel® solution into the gaps. Following vacuum treatment, the Matrigel® solution is pipetted out from the tissue area leaving the Matrigel® in the gaps intact. A confluent layer of endothelial cells is subjected to the leukocytes migration assay in the same manner as before in the presence and absence of fMLP. The migration capability of leukocytes can be compared to obtain a migration vs. shear rate plot.

The experiments described in Example 2 may also be performed in a static mode in which leukocytes are injected into the device and allowed to incubate for 30 minutes. Following incubation, the unbound cells are washed out of the device using cell free media. The devices are then be scanned every 30 minutes for 24 hours to take time-lapse images. At the end of 24 hours, the images are visualized to identify migrated cells. The migration data in absence of fluidic conditions may be compared with that of fluidic conditions to extract the difference between the two procedures. Transient rate of migration of the cells can also be quantified by measuring the distance traversed in the time period.

Experiments may be performed sequentially or simultaneously and may be performed using the same microfluidic chip containing a plurality of devices and/or different microfluidic chips separately or together. Incubation times, flow rates, and reagent concentrations are provided as non-limiting examples and those skilled in the art will appreciate that the precise times, rates, and concentrations used may be and should be varied according to the specific assay and microfluidic chip designs.

EXAMPLE 3

Identifying Agents that Affect Leukocyte Rolling, Adhesion and Migration on Activated Endothelium One or more agents that modulate leukocyte rolling, adhesion, and/or migration may be identified by repeating the experiment in the presence of and/or after pretreatment with one or more candidate agents as in Example 2 in addition to counting migrated cells. Two classes of adhesion molecules involved in the adhesion cascade are selectins and integrins. Antibody-based inhibition of E-selectin reduces leukocyte rolling and antibody-based inhibition of ICAM-1 reduces leukocyte adhesion. Wortmannin, a fungal metabolite has been found to inhibit fMLP dependent migration.

Inhibition of Rolling: Monoclonal antibodies to E-Selectin are injected into the device and allowed to incubate on the endothelial cells for 30 minutes at 37° C. in 5% CO2. Cell free media is flown to wash off unbound antibodies followed by injection of leukocytes into the device. fMLP is injected into the tissue section and rolling, adhesion and migration of the cells are quantified.

Inhibition of Adhesion: Monoclonal antibodies to ICAM-1 are injected and allowed to incubate for 30 minutes followed by a wash to remove unbound antibodies. fMLP is injected as before and rolling, adhesion and migration of the cells are quantified.

Inhibition of Rolling and Adhesion: In this step, both E-selectin and ICAM-1 monoclonal antibodies are incubated together for 30 minutes followed by a wash. Leukocytes are introduced into the device and migration of the cells is quantified in presence of fMLP.

Inhibition of Migration Only: Wortmanin, the fungal metabolite which blocks fMLP dependent migration is mixed with leukocytes at a concentration of 50 nM for 30 minutes at 37° C. Following mixing, leukocytes are injected into the activated device in the presence of fMLP in the tissue sections. Rolling, adhesion and migration of the cells are quantified.

Inhibition of Rolling, Adhesion and Migration: In this step, monoclonal antibodies to E-selectin and ICAM-1 are incubated for 30 minutes. Leukocytes mixed with Wortmanin are injected into the device. Rolling, adhesion and migration of the cells are quantified again in presence of fMLP.

The agent need not be a protein or macromolecule, but may be any small molecule or macromolecule drug candidate with or without a corresponding drug delivery vehicle.

The invention claimed:

1. A method for identifying one or more agents that modulate leukocyte rolling, adhesion, and/or migration comprising the steps of:
    a) flowing a suspension of leukocytes from an inlet of an optically transparent microfluidic chip through a plurality of interconnected flow channels to an outlet;
    b) flowing a solution containing an agent from the inlet of the microfluidic chip through the plurality of interconnected flow channels to the outlet;
    c) locating and counting leukocytes in the microfluidic chip; and
    d) based upon the locations and numbers of leukocytes, determining whether the agent is modulating or not modulating leukocyte rolling, adhesion, and/or migration;

wherein:
    said optically transparent microfluidic chip comprises:
    at least one inlet and at least one outlet;
    a plurality of non-linear, interconnected flow channels having maximum lumenal cross-sections between walls of the flow channels of between 10 and 500 microns, the plurality of non-linear, interconnected flow channels having a geometric characteristic selected from the group consisting of a variable cross-sectional shape, a variable cross-sectional area, a turn, a bend, a bifurcation, a junction, a convolution, an anastomosis, and combinations thereof; and
    at least one tissue space chamber having a maximum cross-sectional dimension of between 100 μm and 1 cm;
    at least a portion of the plurality of interconnected flow channels is porous, said porous portion having pores in the walls of the flow channels with the pores having maximal cross-sections of between 1 and 30 microns; and
    at least one tissue space chamber separate from the interconnected channels and being in fluid communication with the plurality of interconnected flow channels through the pores of said porous portion.

2. The method of claim 1, wherein locating and counting leukocytes is performed by optical means.

3. The method of claim 2, wherein said optical means comprises a camera in communication with an automated stage upon which the microfluidic chip is mounted.

4. The method of claim 1, where the agent that modulates leukocyte rolling, adhesion or migration is selected from the group consisting of cells, liposomes, lipisomes, lipoproteins, microencapsulated drugs, particulate drug carriers, nanoparticles, microparticles, polymer beads, naturally occurring proteins, synthetic proteins, natural compounds, synthetic compounds, and combinations thereof.

5. The method of claim 1, wherein the step of flowing the agent is performed using a flow scheme selected from a single pass, a multiple pass, a recirculating circulation loop, and combinations thereof.

6. The method of claim 1, further comprising the step of measuring a property of the agent, said property selected from the group consisting of real time circulation, stability, half-life, aggregation, degradation, and combinations thereof.

7. The method of claim 1, wherein the step of flowing the solution containing the agent is performed using varying fluidic shear rate values of between 1 sec−1 and 2000 sec−1.

8. The method of claim 1, wherein the solution containing an agent comprises a component selected from the group consisting of serum proteins, whole blood, apheresed blood, eukaryotic cells, bacteria, erythrocytes, viruses, and combinations thereof.

9. The method of claim 1, wherein the flow channels are coated with a confluent layer of cultured endothelial cells.

10. The method of claim 1, wherein the tissue space chamber contains one or more substances selected from the group consisting of an extracellular matrix, a basement membrane, a synthetic matrix, natural occurring matrix, a cytokine, a cell that secrete a cytokine, a gel, a cell culture, a source of a leukocyte chemoattractant, and combinations thereof.

11. The method of claim 1, wherein method steps a) and b) are performed simultaneously or method step (b) is performed before method step (a).

12. The method of claim 1, and further comprising the method step of determining a correlation between flow rate and shear rate for the device and using the determined correlation to set a flow rate for the step of flowing a suspension of leukocytes from the inlet of the device to the outlet.

13. The method of claim 1, wherein said plurality of interconnected flow channels forms a synthetic microvascular network.

14. The method of claim 1, wherein said plurality of interconnected flow channels forms an idealized microvascular network.

15. An optically transparent microfluidic chip comprising:
a) at least one fluid inlet and at least one fluid outlet;
b) a network of non-linear, interconnected flow channels in fluid communication with the at least one fluid inlet and the at least one fluid outlet, each of said flow channels having a maximum cross-section of between 10 and 500 µm; and
c) a tissue space chamber having a maximum cross-sectional dimension of between 100 µm and 1 cm;
wherein:
at least one of the interconnected flow channels includes at least one porous wall that separates the interconnected flow channels from the tissue space chamber and forms a boundary of the tissue space chamber, and the tissue space chamber is in fluid communication with the at least one interconnected flow channel through the pores of the porous wall, the pores having maximum cross-sections of between 1 and 30 µm, the network of non-linear, interconnected flow channels having a geometric characteristic selected from the group consisting of a variable cross-sectional shape, a variable cross-sectional area, a turn, a bend, a bifurcation, a junction, a convolution, an anastomosis, and combinations thereof.

16. The microfluidic chip of claim 15, wherein the interconnected flow channels form a synthetic microvascular network.

17. The microfluidic chip of claim 15, wherein the synthetic microvascular has a geometry identical to one of: a digitized physiological microvascular network or an average of two or more digitized physiological microvascular networks.

18. The microfluidic chip of claim 15, wherein the interconnected flow channels form an idealized microvascular network.

19. The microfluidic chip of claim 18, wherein the interconnected flow channels comprise bifurcation angles of between 15 and 135°.

20. The microfluidic chip of claim 18, wherein the interconnected flow channels comprise of asymmetric or symmetric branching and cross-sections.

21. The microfluidic chip of claim 15 further comprising one or more ports configured to allow fluid to enter and/or exit a lumen of the tissue space chamber.

22. The microfluidic chip of claim 15, wherein the pores are filled with a substance selected from the group consisting of a gel, a basement matrix, an extracellular matrix, a tissue matrix, a synthetic matrix, natural occurring matrix, and combinations thereof.

23. The microfluidic chip of claim 15, wherein luminal surfaces of the flow channels are coated with a layer of cells.

24. The microfluidic chip of claim 15, wherein luminal surfaces of the flow channels are coated with a substance selected form the group consisting of a protein, a proteoglycan, a chemical moiety, and a biomolecule.

25. The microfluidic chip of claim 15, wherein the tissue space chamber contains one or more substances selected from the group consisting of an extracellular matrix, a basement membrane, a cytokine, a cell that secrete a cytokine, a gel, a cell culture, a source of a leukocyte chemoattractant, and combinations thereof.

26. An apparatus comprising the microfluidic chip of claim 15;
pumping means configured to move fluid from the at least one inlet to the at least one outlet; and
optical detection means configured to locate and count cells within the microfluidic chip.

27. An optically transparent microfluidic chip comprising:
a) a fluid inlet and a fluid outlet;
b) at least one non-linear flow channel in fluid communication with the fluid inlet and the fluid outlet, said flow channels having a maximum cross-section of between 10 and 500 µm; and
c) a tissue space chamber having a maximum cross-sectional dimension of between 100 µm and 1 cm;
wherein:
the flow channel includes at least one porous wall that separates the flow channel from the tissue space chamber and forms a boundary of the tissue space chamber, and the tissue space chamber is in fluid communication with the flow channel through the pores of the porous wall, the pores having maximum cross-sections of between 1 and 30 µm, the at least one non-linear flow channel has a geometric characteristic selected from the group consisting of a variable cross-sectional shape, a variable cross-sectional area, a turn, a bend, a bifurcation, a junction, a convolution, an anastomosis, and combinations thereof.

* * * * *